United States Patent [19]

Mabuchi

[11] Patent Number: 4,513,737
[45] Date of Patent: Apr. 30, 1985

[54] BEAUTY TREATMENT DEVICE

[75] Inventor: Kenichi Mabuchi, c/o Mabuchi Motor Co., Ltd. 14-11, Tateishi 3-chome, Katsushika-Ku, Tokyo, Japan

[73] Assignee: Kenichi Mabuchi, Japan

[21] Appl. No.: 219,360

[22] Filed: Dec. 22, 1980

[30] Foreign Application Priority Data

Dec. 29, 1979 [JP] Japan .................... 54-171725
Mar. 10, 1980 [JP] Japan .................... 55-30712[U]

[51] Int. Cl.³ .................................................. A61H 7/00
[52] U.S. Cl. ............................................ 128/52; 128/55
[58] Field of Search ............... 128/52, 51, 55, 24.2; 273/108

[56] References Cited

U.S. PATENT DOCUMENTS

| | | | |
|---|---|---|---|
| 1,352,894 | 9/1920 | Hoffine | 128/51 |
| 1,516,717 | 11/1924 | Coleman | 128/52 |
| 1,545,027 | 7/1925 | Ashlock | 128/52 |
| 1,660,821 | 2/1928 | Sweetland | 128/52 |
| 3,587,588 | 6/1971 | Murr | 128/52 |
| 3,837,335 | 9/1974 | Teranishi | 128/55 |
| 4,055,343 | 10/1977 | Stuart | 273/108 |
| 4,088,128 | 5/1978 | Mabuchi | 128/52 |

*Primary Examiner*—Richard C. Pinkham
*Assistant Examiner*—T. Brown
*Attorney, Agent, or Firm*—McGlew and Tuttle

[57] ABSTRACT

A beauty treatment device comprising a device body, a drive unit housed in the device body, an actuator reciprocated by the drive unit, a patter, or patter assembly removably fitted to the actuator, a space guide fitted to the device body to control the reciprocating motion of the patter assembly, and a resilient member fitted to either or both of the patter assembly and the actuator, compressed as the patter advances towards the open end of the space guide and pats a skin surface being patted, wherein the reciprocating patter repeatedly pats the skin surface at a given rate, whereby removing subcutaneous fat and stimulating subcutaneous muscular tissues to prevent the skin surface to be loosened.

2 Claims, 27 Drawing Figures

BEAUTY TREATMENT DEVICE

BACKGROUND OF THE INVENTION

1. Field of the Invention

This invention relates generally to a beauty treatment device, and more specifically to a beauty treatment device having a space guide that permits an actuator to repeatedly reciprocate and controls the motion of the actuator wherein a patter repeatedly pats a skin surface being treated at a given rate.

2. Description of the Prior Art

It is a wide-spread practice as beauty treatment to repeatedly tap or pat the skin surface with fingertips or palms. Conventionally, various apparatuses have been invented to produce similar face-lifting effects, in which included are an apparatus for applying vibrations to the skin surface and an apparatus for patting part of the body.

The vibrator, however, only presses and/or kneads the skin, causing the skin to stretch. This may result in loosening of the skin or wrinkles in some cases. On the other hand, the conventional patting device which is intended mainly for the massage of the mascular tissues, not for beauty treatment of the skin. In this sense, the conventional patting device belongs to the category of massager.

SUMMARY OF THE INVENTION

It is an object of this invention to provide a beauty treatment device which repeatedly pats the skin by causing a patter or patter assembly to hit the skin at a given rate to impact the skin surface.

It is another object of this invention to provide a beauty treatment device having such a construction that a space guide is provided to maintain a distance between a device body and the skin surface being patted, and both a plate member and a cushion member comprising a patter assembly fitted to an actuator are adapted to protrude slightly from the end face of the space guide.

It is still another object of this invention to provide a beauty treatment device in which the entire patter assembly is removably fitted to the actuator that produces a reciprocating motion.

It is still another object of this invention to provide a beauty treatment device having patters of different shapes which are interchangeably used in accordance with the skin portions being treated.

These and other objects of this invention will become apparent from the following description of embodiments with reference to the accompanying drawings.

DETAILED DESCRIPTION OF THE EMBODIMENTS

Figure 1:
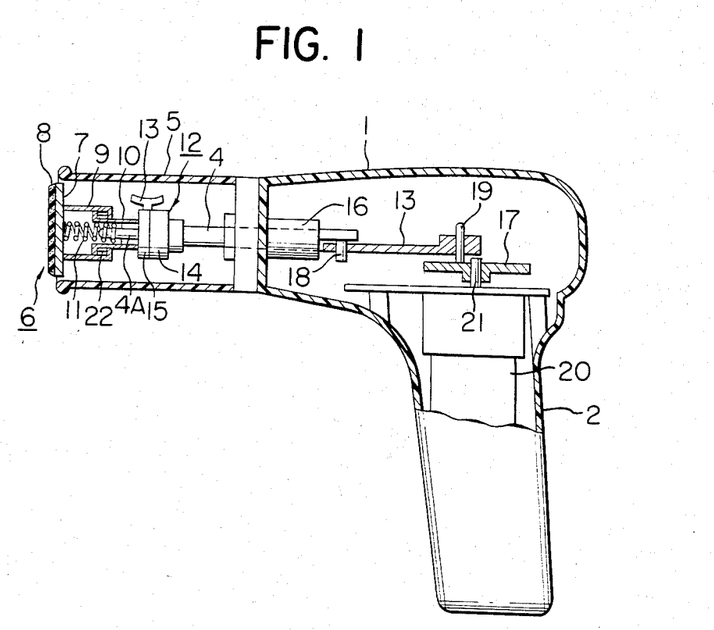
FIG. 1 is a partially sectional side elevation of a beauty treatment device according to this invention.

A beauty treatment device of this invention has a handle 2 fitted to a device body to form the entire device into a pistol shape, as shown in FIG. 1 illustrating an embodiment of this invention. In the handle 2, housed is a motor 20 which causes a motor output shaft 21 to rotate via a reduction gear (not shown) fitted thereto as necessary. A rotating disc 17 is fixed to the motor output shaft 21, which in turn causes the rotating disc 17 to rotate. A rod 3 is fitted at an end thereof to a crankshaft 19 provided on the rotating disc 17, the other end thereof being connected to an actuator 4 via a rod shaft 18. Consequently, as the rotating disc 17 rotates, the actuator 4 is caused to reciprocate within an actuator bearing 16 via the rod 3.

Figure 8:
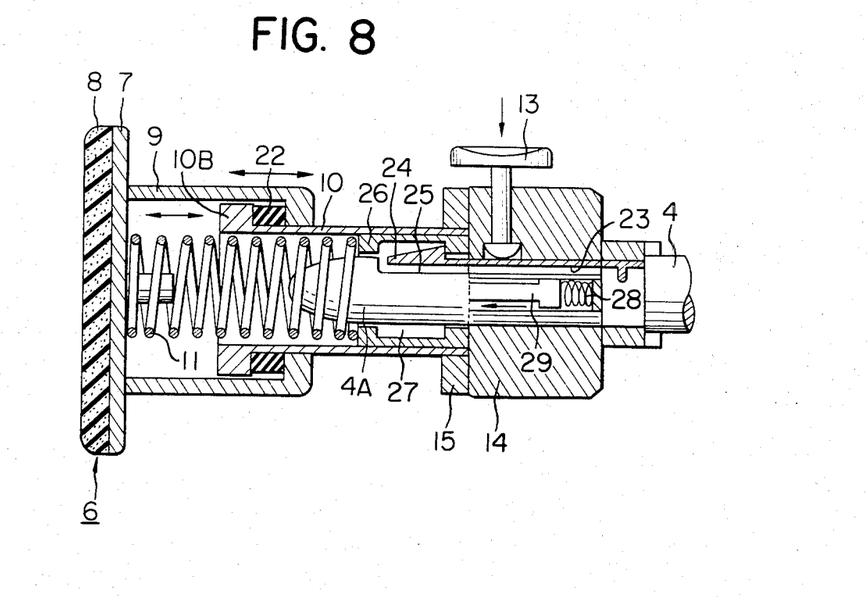
FIG. 8 is a crosssectional view illustrating a resilient member of this invention housed in a device body and a form of patter connecting mechanism according to this invention.

In this Specification, a patter, or patter assembly 6 comprises a plate member 7, a cushion member 8, a patter body 9, a patter slide tube 10 etc. The patter, or patter assembly 6 is connected to the actuator 4 by means of a patter connecting mechanism 12, which will be described later, referring to FIG. 8. More specifically, as the actuator 4 is connected to the patter slide tube 10 via the patter connecting mechanism 12, the reciprocating motion of the actuator 4 is transmitted directly to the patter slide tube 10. The patter slide tube 10 is slidably fitted to the patter body 9. Inside the patter body 9, disposed is a resilient member 11, which depresses the plate member 7 fitted to the patter body 9 and an end face of an actuator head supporting tube 26 press-fitted into the patter slide tube 10, as shown in FIG. 8. Consequently, the reciprocating motion of the patter slide tube 10 is also directly transmitted to the patter body 9 by resiliency of the resilient member 11. A cushion member 8 fitted to the plate member 7 hits the skin surface at the front surface thereof, giving an impact to the skin surface. At the left end (in the figure) of the patter slide tube 10 slidably fitted to the patter body 9, provided is a flange 10B which slides within the inside surface of the patter body 9. The flange 10B makes contact with the closed end of the patter body 9 via a cushioning rubber 22, causing the patter body 9 to move to the right (in the figure) when the patter slide tube 10 is moved to the right.

When a force is applied to the patter slide tube 10 in the leftward direction, the patter slide tube 10 is moved to the left, together with the resilient member 11 which pushes the left end face of the actuator head supporting tube 26 press-fitted into the patter slide tube 10.

When the plate member 7 is prevented from being moved leftward as the cushion member 8 strikes the skin surface, the resilient member 11 is compressed. And, the patter slide tube 10 slides leftward with respect to the patter body 9. As a result, the plate member 7, after giving an impact to the skin surface at a given speed, pushes the skin surface by resiliency of the compressed resilient member 11. The right-hand pushing surface of the resilient member 11 may make contact with the left end face of the patter slide tube 10, instead of the actuator head supporting tube 26. The reciprocating motion transmitted to the patter body 9 is also transmitted to the cushion member 8 fitted to the plate member 7. That is, the rotation of the motor 20 is transmitted to the actuator 4 in the form of reciprocating motion, which is in turn transmitted to the plate member 7 and the cushion member 8. In other words, the rotation of the motor 20 causes the plate member 7 and the cushion member 8 to repeatedly reciprocate. With this reciprocating motion, the cushion member 8 repeatedly pats the skin surface.

In general, the velocity v of the actuator 4 is given by the following equation.

$$V \approx r \cdot \{\sin \theta - (\lambda/2) \sin 2\theta\} \cdot \omega \qquad (1)$$

where
 r: radius of crankshaft 19
 l: length of rod 3
 $\theta$: rotating angle of rotating disc 17 (the rotating angle $\theta$ in a state where the patter assembly 6 is retracted farthest from the open end of the space guide 5 is assumed to be 0.)
 $\omega$: angular velocity of rotating disc 17
 $\lambda$: r/l As is evident from this equation, when $\theta = \pm n\pi$ (n=0,1, 2..) the velocity of the actuator 4 becomes zero. Consequently, in order to cause the cushion member 8 of the patter assembly 6 to strike the skin surface at a given speed, the rotating angle of the rotating disc 17 must satisfy $\theta \neq \pm n\pi$.

In the beauty treatment device of this invention, therefore, the cushion member 8 is adapted to strike the skin surface in a state where the rotating disc 17 is at a predetermined rotating angle $\theta$ and the resilient member 11 is compressed during the period where the rotating angle $\theta$ reaches $\pi$.

Figure 2:
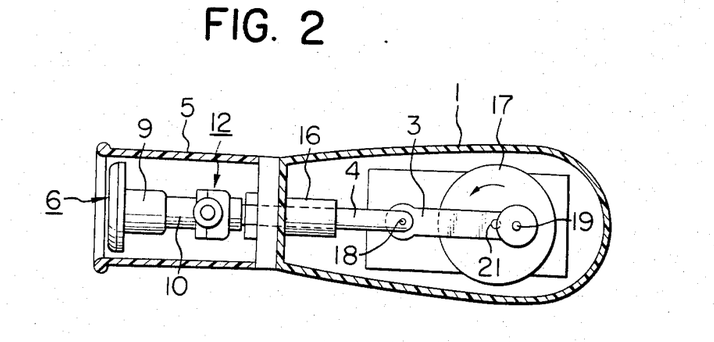
FIGS. 2 through 5 are sectional plan views of assistance in explaining the action of the beauty treatment device of this invention.
Figure 3:
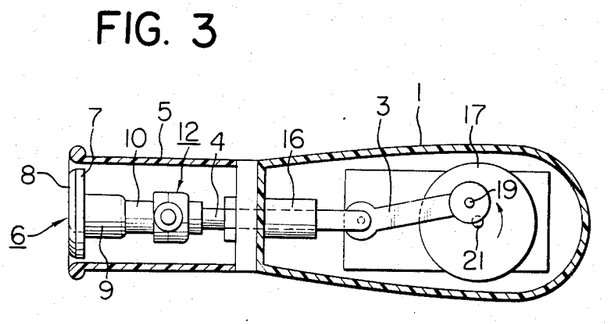

FIG. 2 shows the state where the patter assembly 6 is at the farthest location from the open end of the space guide 5. As is evident from the figure, the rotating angle $\theta$ of the rotating disc 17 is zero. The velociy v of the patter assembly 6 is therefore zero from the equation (1). In this state, the actuator 4 is moved to the extreme right side. The relative position of the patter body 9 and the patter slide tube 10 slidably fitted to the patter body 9 is such that the flange 10B of the patter slide tube 10 is located at the farthermost position from the plate member 7, as shown in FIG. 8. As the rotating disc 17 rotates from the state shown in FIG. 2 to the state shown in FIG. 3, or as the cushion member 8 of the patter assembly 6 becomes flush with the open end face of the space guide 5, the patter assembly 6 is moved at the velocity v given by the equation (1). That is, the cushion member 8 of the patter assembly 6 strikes the skin surface at the velocity v so long as the skin surface being treated exists at the open end face of the space guide 5. Until this moment, the relative position of the patter body 9 and the patter slide tube 10 remains essentially unchanged from the state shown in FIG. 2.

Figure 4:
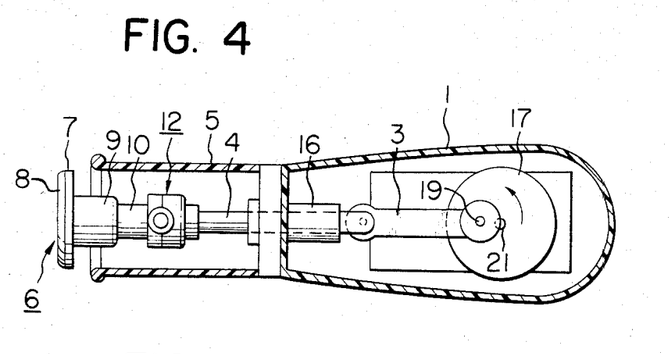
Figure 5:
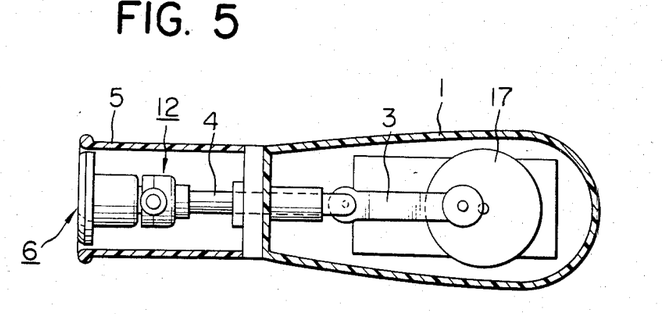

FIG. 4 shows the state where the rotating disc 17 further rotates until the rotating angle $\theta$ becomes $\pi$, with no skin surface exists at the open end face of the space guide 5. In this state, the actuator 4 assumes the extreme left-hand position, and the cushion member 8 of the patter assembly 6 protruding from the open end face of the space guide 5, as shown in FIG. 4. The velocity v of the patter assembly 6 at this position is zero, and the relative position of the patter body 9 and the patter slide tube 10 is the same as that shown in FIGS. 2 and 3. If the skin surface being treated exists at the open end face of the space guide 5, the patter assembly 6 cannot protrude from the space guide 5 as shown in FIG. 4. As a result, the cushion member 8 of the patter assembly 6 stops at a position flush with or slightly above the open end face of the space guide 5, as shown in FIG. 5. FIG. 5 shows the state where the rotating disc 17 is at the rotating angle $\theta = \pi$, with the actuator 4 being moved to the extreme left side. The patter body 9 of the patter assembly 6 which is prevented form being moved leftward by the skin surface remains at the same position during the time from the moment at which the patter assembly 6 of FIG. 3 strikes the skin surface to the moment at which the state shown in FIG. 5 is reached. On the other hand, the patter slide tube 10 is moved leftward via a patter connecting mechanism 12 as the actuator 4 moves leftward. That is, the patter slide tube 10 slidably fitted to the patter body 9, as shown in FIG. 8, is moved leftward (in the figure), resisting the resiliency of the resilient member 11. Consequently, in FIG. 5 where the actuator 4 is moved to the extreme left-hand position, or where the rotating angle $\theta$ of the rotating disc 17 is $\pi$, the resilient member 11 is almost completely compressed. In this way, the distance between the patter body 9 and the patter slide tube 10 can be flexible adjusted, permitting the rotating disc 17 to rotate even when the patter assembly 6 is prevented from being protruded from the end face of the space guide 5 by the skin surface.

Thus, the invention comprises a housing 2 with a crank member in the form of disk 17 with crank shaft 19 rotatably mounted about a center of rotation at motor shaft 21. An actuator in the form of acatatuator 4 and connecting shaft 13, has one end rotatably mounted on crank shaft 19, at an eccentric radial location on crank member 17, with an opposite end of the actuator slidaby mounted with respect to the housing 2 for motion in a linear stroke with rotation of the crank member 17. The actuator has an extended dead center position shown in FIG. 1, with a patter connected to the outer opposite end of the actuator. Resilient means in the form of the body 9 and spring 11 are connected between the actuator and the patter, or somewhere on the actuator or the patter, to extend the patter beyond the spacer 5 in the extended dead center position of the actuator. In this way, the patter contacts the skin before the actuator has reached its extended dead center position so that there is still some velocity at the patter when it contacts the skin.

Figure 6:
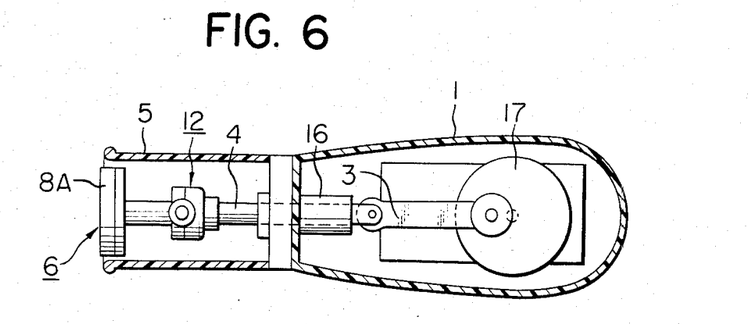
FIGS. 6 through 7 are sectional plan views of other embodiments of this invention of assistance in explaining the action of the beauty treatment device of this invention.
Figure 7:
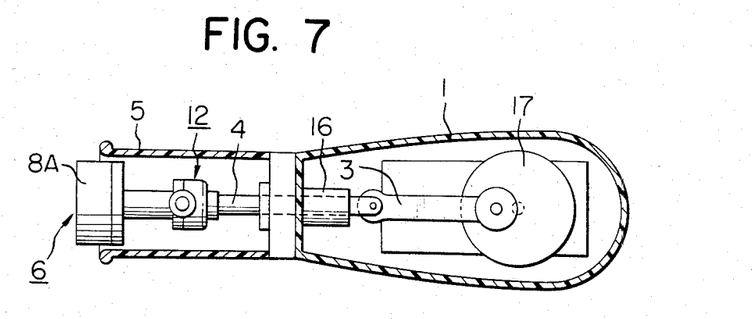

FIGS. 6 and 7 are diagrams illustrating another embodiment of the beauty treatment device according to this invention, where a cushion member 8A is fitted to the plate member 7 to substitute for the resilient member 11 that is compressed while the patter assembly 6 strikes the skin surface. FIG. 6 shows the state where the cushion member 8A is compressed into a rigid form. The cushion member 8A is disposed so that the surface of the cushion member 8A, when compressed, is flush with or slightly above the end face of the space guide 5. FIG. 7 shows the state where the cushion member 8A is allowed to expand.

As the rotating disc 17 begins rotating from the position where $\theta = 0$, reaching a predetermined rotating angle, the end face of the cushion member 8A of the patter assembly 6 hits the skin surface on the end face of the space guide 5. Then, the cushion member 8A begins to be compressed, and continues to be compressed until the rotating disc 17 further rotates to the position where $\theta = \pi$, as shown in FIG. 6. Thanks to this distance adjusting function of the cushion member 8A, the plate member 7 can continue to pat the skin surface at a given speed.

As is apparent from the above description, the distance adjusting function of a resilient member provided on either of the patter assembly 6 and the actuator 4 permits the patter assembly 6 to repeatedly pat the skin surface.

In the invention, the space guide 5 plays a role of maintaining the distance between the device body 1 and the skin surface constant. In the absence of the space guide 5, the patting intensity of the patter assembly 6 would become unstable due to the variability of the distance with service conditions. In other words, it would become difficult for the patter assembly 6 to pat the skin surface at a constant rate. In some cases, the absence of the space guide 5 would cause both the plate member 7 and the cushion member 8 to be kept in contact with the skin surface at all times to exert a pushing force onto the skin surface, rather than patting the skin.

As described above, the beauty treatment device of this invention makes it possible to remove subcutaneous fat, stimulate subcutaneous mascular tissues and prevent the skin from loosening or wrinkling by patting the skin surface with the patter assembly 6. In addition, these effects can be enhanced by changing the shape or patting intensity of the patter assembly 6 or using a magnet as a part of the patter assembly 6 in accordance with the portion being treated or the purpose of treatment. To achieve this, the patter assembly 6 requires to be interchangeable. Furthermore, the patter assembly 6 must be securely connected to the actuator 4 to prevent unwanted disengagement.

The beauty treatment device of this invention, therefore, has a patter connecting mechanism for facilitating the changing of the patter assembly 6, some forms of which are shown in FIGS. 8 through 20.

Figure 9:
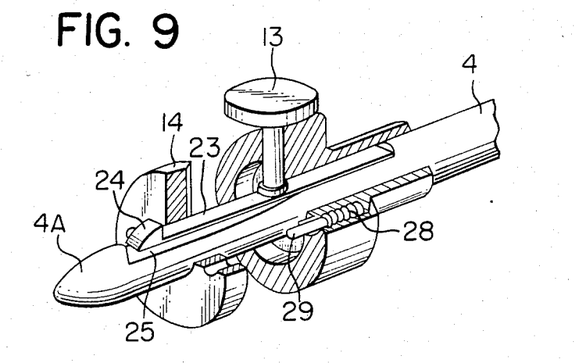
FIG. 9 is a perspective view of assistance in explaining the method of fitting and removing the patter connecting mechanism shown in FIG. 8.

In an example of the connecting mechanism of this invention shown in FIGS. 8 and 9, a clearance groove 25 is provided on the actuator head 4A so as to permit a leaf spring 23 equipped with a patter connecting pawl 24 to be lowered, and the tip of the actuator head 4A is formed into a rounded cone shape. The leaf spring 23 having at the tip thereof the patter connecting pawl 24 is fitted to the actuator 4 above the clearance groove 25. The actuator 4 is press-fitted to a coupling 14 to which a patter engaging/disengaging button 13 is slidably fitted, as shown in FIG. 8. The coupling 14 has a hole into which a patter ejecting pin 29 and a spring 28 are inserted. The cut-away view of the coupling 14 is shown in FIG. 9, with the coupling 14 separated into front and rear halves. (Although FIG. 9 shows the coupling 14 separated into halves for ease of understanding, the actual coupling 14 is formed into one piece.) Furthermore, an actuator head supporting cylinder 26 having a pawl groove 27 for engaging with the patter connecting pawl 24 is press-fitted into the patter slide tube 10. The actuator head supporting cylinder 26 functions to connect the actuator 4 and the patter assembly 6. FIG. 8 shows the state where the patter assembly 6 is connected to the actuator 4. To change the patter assembly 6, the patter engaging/disengaging button 13 is depressed to cause the left spring 23 to be lowered into the clearance groove 25. This in turn lowers the patter connecting pawl 24 provided at the tip of the leaf spring 23 to disengage from the pawl groove 27 provided on the actuator head supporting cylinder 26. With this, the patter assembly 6 is disconnected from the actuator 4. As a result, a flange 15 fixed to the outer periphery of the patter slide tube 10 is pushed leftward in the figure by the patter ejecting pin 29 which keeps pushing the flange 15 at all times by the resiliency of the spring 28 to eject the patter assembly 6 form the actuator 4. When mounting the patter assembly 6, the actuator head 4A is inserted into the patter slide tube 10 of the patter assembly 6. This causes the patter connecting pawl 24 to engage with the pawl groove 27 of the actuator head supporting cylinder 26. Thus, the patter assembly 6 is connected to the actuator 4. The patter assembly 6 can be connected to the actuator 4 at any angular position since the pawl groove 27 for engaging with the patter connecting pawl 24 is provided in an annular shape along the inner periphery of the actuator head supporting cylinder 26. In this state, the patter ejecting pin 29 is pushed backward by the flange 15 and retracted into the coupling 14, resisting the force of the spring 28. In this way, the patter assembly 6 can be easily changed.

Figure 10:
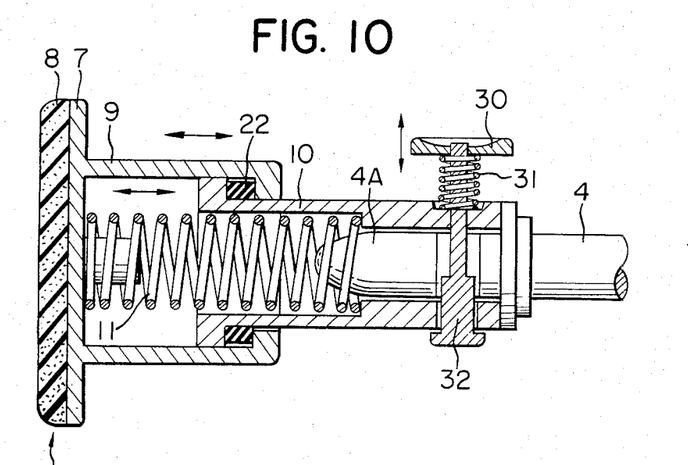
FIG. 10 is a crosssectional view illustrating the resilient member of this invention housed in the device body and another form of patter connecting mechanism of this invention.
Figure 11:
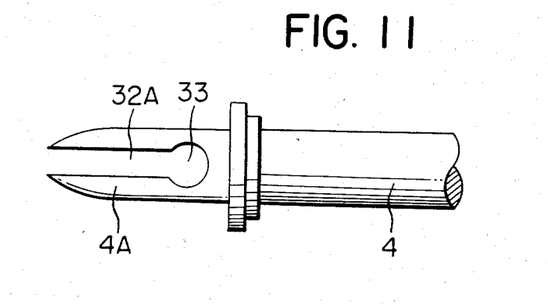
FIG. 11 is a plan view of the head portion of the actuator shown in FIG. 10.
Figure 12:
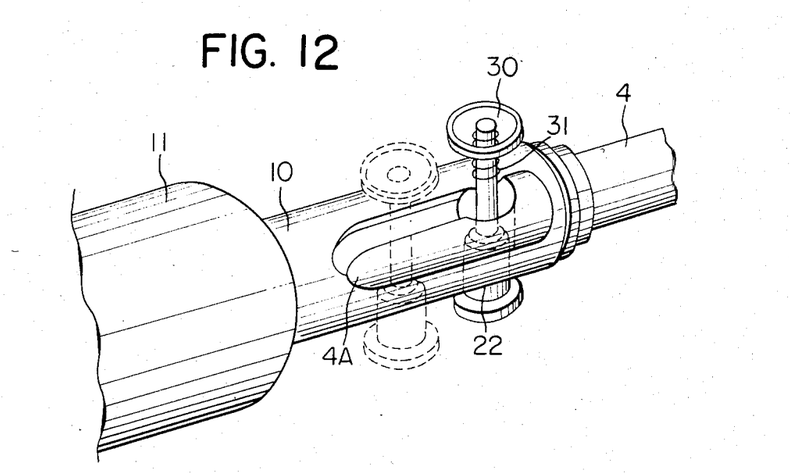
FIG. 12 is a perspective view of assistance in explaining the method of fitting and removing the patter connecting mechanism shown in FIG. 10.

FIGS. 10 through 12 show another example of the patter connecting mechanism according to this invention where a slot 32A and a connecting pin hole 33 are provided on the actuator head 4A and a connecting pin 32 having shanks of different diameters is provided. The slot 32A is formed so as to permit the small diameter shank of the connecting pin 32 to pass but does not permit the large diameter shank to pass, and the connecting pin hole 33 is formed slightly larger than the large diameter shank of the connecting pin 32. The connecting pin 32 is slidably fitted to the patter slide tube 10 of the patter assembly 6 through a hole provided across the diameter of the patter slide tube 10, and a pushbutton 30 is fitted to an end of the connecting pin 32 with a spring 31 interposed between the pushbutton 31 and the patter slide tube 10. When changing the patter assembly 6, the pushbutton 30 is depressed to lower the connecting pin 32 so as to permit the small diameter shank of the connecting pin 32 to pass through the slot provided on the actuator head 4A. This connecting mechanism has directionality in connecting the patter assembly 6 and the actuator 4 since the connecting pin 32 must be aligned with the connecting pin hole 33.

Figure 13:
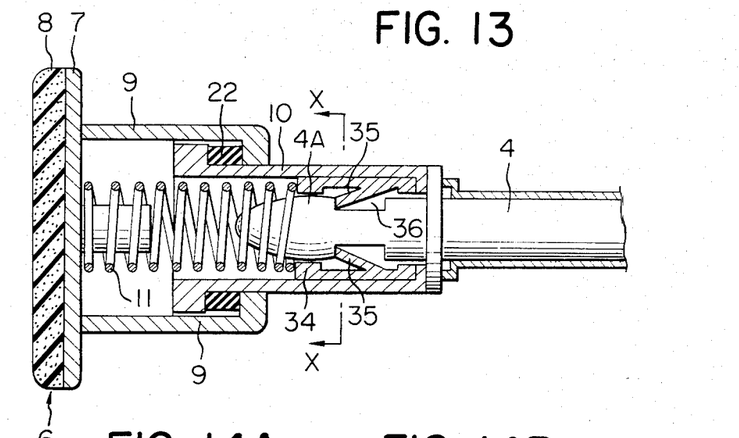
FIG. 13 is a crosssectional view of another form of patter connecting mechanism of this invention.
Figure 14A:
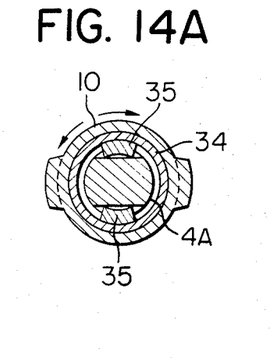
FIGS. 14A and 14B are diagrams of assistance in explaining the method of fitting and removing the head portion of the actuator shown in FIG. 13.
Figure 14B:
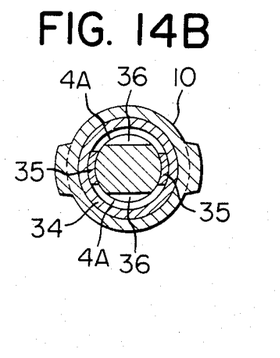

FIGS. 13 and 14 show another example of the connecting mechanism of this invention where resilient connecting pawls 35 are provided inside the patter slide tube 10 of the patter assembly 6, and pawl grooves 36 are provided on the actuator head 4A. FIG. 14A is a crosssectional view of the connecting mechanism shown in FIG. 13 taken along the line X—X, a FIG. 14B is a diagram of assistance in explaining the engaging and disengaging operation of the patter assembly 6.

A resilient connecting pawl supporting cylinder 34 having resilient connecting pawls 35 is press-fitted into the patter slide tube 10. On the actuator head 4A, provided are pawl grooves 36 for engaging with the resilient connecting pawls 35. The patter assembly 6 is connected to the actuator 4 by engaging the resilient connecting pawls 35 with the pawl grooves 36. When disengaging the patter assembly 6 from the actuator 4, the patter slide tube 10 or the actuator 4 in the state shown in FIGS. 13 and 14A is turned 90° to obtain the state shown in FIG. 14B. In this state, the patter assembly 6 can be easily disconnected from the actuator 4 because the resilient connecting pawls 35 are disengaged from the pawl grooves 36. With this linkage, the relative angular position of the actuator 4 and the patter assembly 6 must be properly matched.

Figure 15:
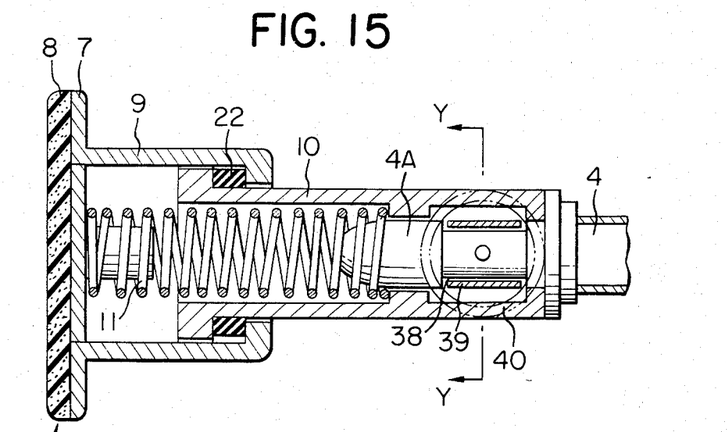
FIG. 15 is a crosssectional view of another form of patter connecting mechanism of this invention.
Figure 16:
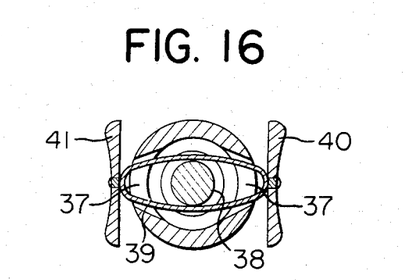
FIG. 16 is a diagram of assistance in explaining the method of fitting and removing the head portion of the actuator shown in FIG. 15.

FIGS. 15 and 16 show another example of the connecting mechanism according to this invention where an elliptical leaf spring 39 is inserted in the patter slide tube 10 and a spring groove 38 is provided on the actuator head 4A. FIG. 16 is a crosssectional view of the connecting mechanism shown in FIG. 15 taken along the line Y—Y.

A spring hole 37 is provided on the patter slide tube 10, into which the elliptical leaf spring 39 is inserted. At both ends of the elliptical leaf spring 39, fitted are pushbuttons 40 and 41 for compressing the elliptical leaf spring 39. On the other hand, a spring groove 38 for securing the actuator 4 by means of the elliptical leaf spring 39 is provided on the actuator head 4A. The elliptical leaf spring 39 engages with the spring groove 38 to hold the actuator 4 in position. When disconnecting the patter assembly 6 from the actuator 4, the pushbuttons 40 and 41 are depressed to compress the elliptical leaf spring 39 into a circular shape to cause the spring 39 to be disengaged from the spring groove 38. This mechanism has no directionality in connecting or disconnecting the actuator 4 and the patter assembly 6. In other words, the patter assembly 6 can be connected to the actuator 4 at any angular position.

Figure 17:
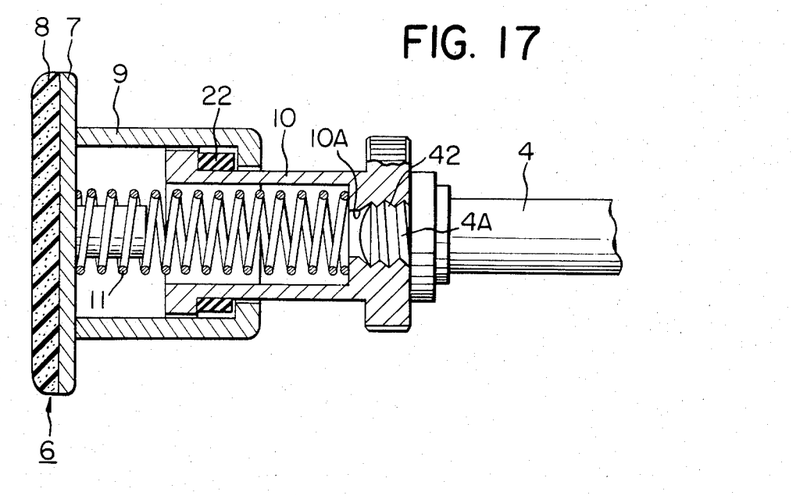
FIG. 17 is a crosssectional view of another form of patter connecting mechanism of this invention.

FIG. 17 shows another example of the patter connecting mechanism according to this invention where the patter assembly 6 is screwed on the actuator 4.

A female thread 10A is provided on the inside surface of the patter slide tube 10 while a male thread 42 is provided on the actuator head 4A. The patter assembly 6 and the actuator 4 can be connected to each other more effectively and positively by using a resilient member for preventing the loosening of the connection.

Figure 18:
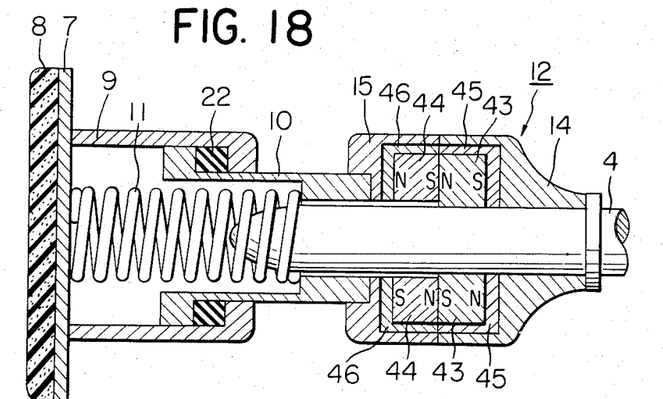
FIG. 18 is a crosssectional view of still another form of patter connecting mechanism of this invention.
Figure 19:
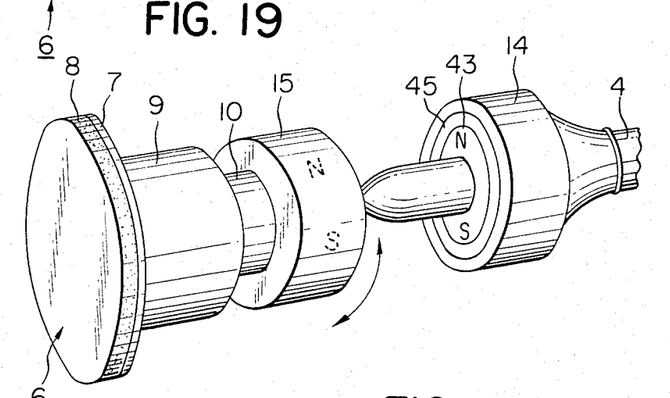
FIG. 19 is a perspective view of assistance in explaining the method of fitting and removing the patter connecting mechanism shown in FIG. 18.

FIGS. 18 and 19 show other embodiments of this invention where reference numerals 43 and 44 refer to magnets; 45 and 46 to yoke cores provided on the outer periphery of the magnets 43 and 44.

As shown in FIGS. 18 and 19, the magnet 43 is implanted in the coupling 14, with polarity at the end face thereof being disposed as shown in the figures. The magnet 44 is also implanted in the flange 15 fixed to the end of the patter slide tube 10, with polarity at the end face thereof being disposed in such a manner that the number and position of the poles of the magnet 44 correspond with those of the magnet 43.

As shown in FIG. 18, the magnet 43 implanted in the coupling 14 and the magnet 44 implanted in the flange 15 are connected to each other by attracting force caused by different polarities on the two magnets 43 and 44. In this state, or in the state where the actuator 4 is connected to the patter assembly 6, the patter assembly 6 is operated, as described referring to FIGS. 1 through 5. To change the patter assembly 6, the coupling 14 or the flange 15 or both are turned in either direction shown by arrows shown in FIG. 19. By turning 180° in FIG. 19, for example, the magnet 43 implanted in the coupling 14 and the magnet 44 implanted in the flange 15 are repulsed with each other due to repulsion force caused by the same polarities, causing the patter assembly 6 to separate from the actuator 4.

When connecting the patter assembly 6 to the actuator 4, the end face of the actuator is brought in close contact with the end face of the flange 15. This causes the magnet 43 implanted in the coupling 14 and the magnet 44 implanted in the flange 15 to attract with each other, bringing the actuator 4 and the patter assembly 6 in position.

This connecting mechanism 12 utilizing the different polatities of the magnets 43 and 44 ensures positive connection of the actuator 4 and the patter assembly 6, both of which are subjected to vibrations caused by high-speed reciprocating motion. In addition, positive connection can be ensured without positioning the actuator 4 and the patter assembly 6.

The changing of the patter assembly 6 can be easily accomplished since the actuator 4 and the patter assembly 6 are automatically disconnected merely by turning each other.

Figure 20:
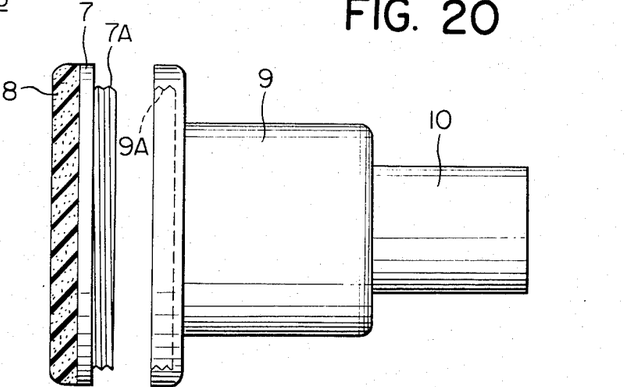
FIG. 20 is a diagram illustrating the mechanism of changing cushion members in a beauty treatment of this invention.

FIG. 20 is a diagram illustrating the mechanism of changing the cushion member 8 in the beauty treatment device of this invention where a male screw thread 7A is provided on the plate member 7 while a female screw thread 9A is provided on the patter body 9.

This screw-in mechanism for connecting the plate member 7 to the patter body 9 is convenient not only in changing the cushion member 8 but also in assembling the patter slide tube 10.

Figure 21A:
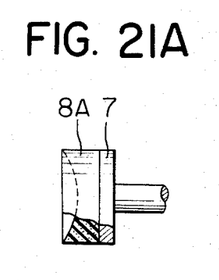
FIGS. 21A through 21C and 22A through 22C are side elevations of various modified forms of the patter according to this invention.
Figure 21B:
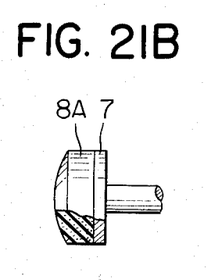
Figure 21C:
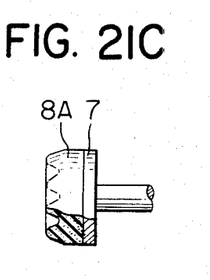

FIGS. 21A through 21C show examples of patter assemblies that can be used interchangeably in accordance with the portion or purpose of treatment.

Figure 22A:
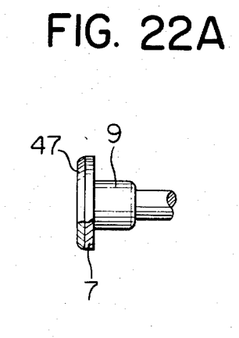
Figure 22B:
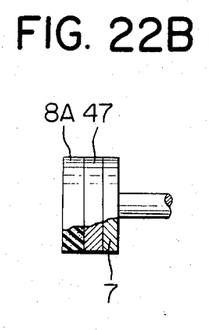
Figure 22C:
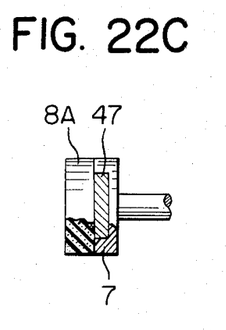

FIGS. 22A through 22C show examples of patter assemblies to be used in the beauty treatment device of this invention, on which a magnet are mounted in place of the cushion member 8 or in between the plate member 7 and the cushion member 8. Bu using the patter assembly 6 equipped with a magnet, not only an effect of patting the skin surface but also an effect of inducing a small current in blood by electromagnetic induction caused by changes in magnetic field on the skin surface resulting from the reciprocating motion of the magnet mounted on the patter assembly can be expected. The example shown in FIG. 22A is a patter assembly having a magnet 47 in place of the cushion member 8. FIGS.

22B and 22C show patter assemblies having a magnet 47 interposed between the cushion member 8 and the plate member 7.

The patter assembly to be used in the beauty treatment device is not limited to the examples shown in FIGS. 21 and 22, but may be a combination of the example shown in FIG. 21C and that shown in FIG. 22B, for example. In using the beauty treatment device of this invention, it is desirable to change the patting intensity of the patter assembly according to the portion and purpose of treatment. Needless to say, the desired patting intensity can be obtained by using a patter assembly having an appropriate surface area.

As described above, the beauty treatment device of this invention makes it possible to stimulate subcutaneous muscular tissues and prevent the loosening of the skin by repeatedly patting the skin surface at a given speed. In addition, the beauty treatment device of this invention is capable of easily changing the patter assembly and immune to vibrations. Furthermore, better treatment effects can be obtained by selecting a proper patter assembly having a desired shape or size, or equipped with a magnet according to the portion or purpose of treatment.

What is claimed is:

1. A beauty treatment device for treating a person's body, comprising a housing, an actuator mounted in said housing for sliding to and fro oscillating movement, drive means connected to said actuator to oscillate it, a patter member carried by said actuator and movable therewith, resilient means associated with said patter member and said actuator permitting a resilient give of said patter after contact with the body, a connecting mechanism between said actuator and said patter member permitting separation of said actuator from said patter member, push button means associated with said connecting mechanism for connecting and disconnecting said patter member and said actuator, said push button means including a pawl groove provided on said patter member and a connecting pawl fixed to said actuator and being engageable and disengageable with said pawl groove and a push button movably mounted in said housing being movable to shift said pawl.

2. A patting device for a beauty treatment comprising:
    a housing;
    a crank member rotatably mounted to said housing about a center of rotation;
    an actuator having one end rotatably mounted to said crank member at a fixed eccentric radial location on said crank member, and an opposite end slidably mounted with respect to said housing for executing a positive linear stroke having an extended dead center position, with rotation of said crank member,
    drive means in said housing connected to said crank member for rotating said crank member,
    spacer means connected to said housing and extending in a direction of said linear stroke beyond said actuator opposite end in its extended dead center position, at least a portion of said actuator moving in said spacer means,
    a patter member slidably connected to said actuator at said opposite end thereof; and
    a spring member engaged between said patter member and said actuator for resilient contraction in a direction parallel to said linear stroke, said spring member holding said patter member beyond an end of said spacer means with said actuator in its extended dead center position so that, before said actuator reaches its extended dead center position, said patter member contacts a skin surface to be treated against which said spacer means is held;
    said drive means comprising an electric motor having a shaft connected to said crank member at said center of rotation thereof.

* * * * *